United States Patent [19]

Marsh

[11] Patent Number: 4,555,485
[45] Date of Patent: Nov. 26, 1985

[54] PRODUCTION OF EDIBLE PROTEIN CONTAINING SUBSTANCES

[75] Inventor: Robert A. Marsh, Haddenham, ·reat England

[73] Assignee: Ranks Hovis McDougall, PLC, Berkshire, England

[21] Appl. No.: 593,473

[22] Filed: Mar. 26, 1984

[30] Foreign Application Priority Data

Mar. 24, 1983 [GB] United Kingdom ................. 8308162

[51] Int. Cl.[4] ......................... C12P 21/00; C12R 1/77; A01N 61/00

[52] U.S. Cl. ....................................... 435/68; 435/929; 514/2

[58] Field of Search ........................ 435/68, 929; 514/2

[56] References Cited

U.S. PATENT DOCUMENTS

| | | | |
|---|---|---|---|
| 3,937,654 | 2/1976 | Solomons et al. | 435/929 |
| 3,937,693 | 2/1976 | Towersey | 435/929 |
| 4,061,781 | 12/1977 | Solomons et al. | 435/929 |
| 4,163,692 | 8/1979 | Yates | 435/929 |
| 4,265,915 | 5/1981 | MacLennan et al. | 435/929 |
| 4,294,929 | 10/1981 | Solomons et al. | 435/929 |

FOREIGN PATENT DOCUMENTS

| | | |
|---|---|---|
| 869392 | 11/1941 | France . |
| 1085994 | 10/1967 | United Kingdom . |
| 1346062 | 2/1974 | United Kingdom . |
| 1523583 | 7/1975 | United Kingdom . |
| 1440642 | 6/1976 | United Kingdom . |
| 1502455 | 3/1978 | United Kingdom . |

OTHER PUBLICATIONS

Nature, vol. 287, Sep. 4, 1980, p. 6, Newark.
Chemical Abstracts, vol. 92, (1980), 160287b; Gibb et al.

*Primary Examiner*—Jerome D. Goldberg
*Assistant Examiner*—Joseph A. Lipovsky
*Attorney, Agent, or Firm*—Reising, Ethington, Barnard, Perry & Milton

[57] ABSTRACT

The production of an edible protein-containing substance by continuous fermentation using *Fusarium graminearum* in a culture medium containing all necessary growth promoting nutrient substances. Oxygen constitutes the limiting nutrient and is present to support cell concentration in the culture without the occurrence of anaerobic growth.

4 Claims, No Drawings

PRODUCTION OF EDIBLE PROTEIN CONTAINING SUBSTANCES

BACKGROUND OF INVENTION

The present invention relates to a process for the production of edible protein-containing substances and has particular reference to the production of fungal protein by microbial action.

PRIOR ART

GB No. 1210356 relates to a process for the production of an edible protein-containing substance which comprises incubating which is a non-toxic strain of a micro-fungus of the class Fungi Imperfecti, in a culture medium containing essential growth-promoting nutrient substances, of which carbon in the form of assimilable carbohydrate constitutes the limiting substrate in proliferation, and separating from an assimilable carbohydrate exhausted medium, the proliferated organism which constitutes the edible protein-containing substance.

GB No. 1331471 claims an edible protein-containing substance comprising fungal mycelium possessing a high net protein utilisation value, on rat assays, of at least 70 based on the α-amino nitrogen.

GB No. 1346062 describes a process for the production of an edible protein-containing substance which comprises incubating and proliferating, under aerobic conditions, a non-toxic strain of the genus Fusarium or a variant or mutant thereof, in a culture medium containing essential growth-promoting nutrient substances, of which carbon in the form of assimilable carbohydrate constitutes the limiting substrate in proliferation, and separating the proliferated organism comprising the edible protein-containing substance.

Although the control of the process of producing an edible protein gives the highest yield on carbon when carbon is the limiting nutrient, we have found that the physical properties and eating quality of the edible protein-containing substance can now be improved. These product advantages outweigh the yield loss compared with limitation by carbon.

SUMMARY OF INVENTION

Accordingly, the present invention provides a process for the production of an edible protein-containing substance, which comprises inoculating and operating a continuous fermentation, using *Fusarium graminearum*, in a culture medium containing all necessary growth-promoting nutrient substances, and aerated in such a way that oxygen constitutes the limiting nutrient.

The present invention also provides a non-toxic fungal mycelium of *Fusarium graminearum* capable of being used as a foodstuff for human beings having hyphae of median length greater than 0.3 mm produced from a continuous fermentation of a culture medium containing *Fusarium graminearum* and all necessary growth promoting nutrient substances with oxygen as the limiting nutrient.

The separated proliferated organism comprising the edible protein-containing substance may be incorporated into a foodstuff for human or animal consumption. The process is a development of that described in GB No. 1346062. Our experience of using that process and the products for incorporation into various foodstuffs such an analogues of poultry, fish and meat, as well as sweet and savoury snack products has shown that a problem arises and carbon limitation provides a product made up of branched hyphal strands with median length of 0.25 to 0.3 mm. However, for such products, it has been found that edible protein-containing substance with a longer fibre length can be textured to produce a product which more closely matches the texture of the original foodstuff. By using a fermentation in which oxygen is the limiting nutrient, the product quality is improved. Oxygen limited fermentation generally provides hyphae having a median length of greater than 0.3 mm, usually 0.3 mm–0.5 mm with little or no branching.

Following growth of the edible protein-containing substance, it may be treated by heat shock treatment to reduce the amount of ribonucleic acid (RNA) in the product. A method of RNA-reduction is described in GB No. 1440642. Long hyphal strands, (length 0.3–0.5 mm) which contain little or no branching are desirable for the subsequent texturisation, as described in GB No. 1502455, of RNA reduced and harvested edible protein containing substance in that it allows a greater degree of alignment of hyphae, and a greater perceived fibrousness in the finished product. In addition oxygen limitation produces a harvested RNA-reduced material which is pale buff in colour and essentially bland in odour and flavour. Provided also that the level of oxygen just supports the cell concentration in the culture, no essentially anaerobic metabolism occurs, and a bland odour can be maintained in the harvested material.

The present invention is suitable for continuous fermentation. Oxygen limitation allows hyphae of characteristics desirable for a wide range of end products to be produced, with good productivity in the fermentation vessel. Provided all other nutrients are present in excess, productivities of 3.0 gm $l^{-1}$ $hr^{-1}$ or greater can be maintained.

Oxygen or oxygen enriched air is introduced into the fermenter at atmospheric pressure or greater, for example from 101 $kN/m^2$ to 505 $kN/m^2$. Systems at pressures of 101 $kN/m^2$ to 330 $kN/m^2$ in the fermentation vessel have been studied, with various impeller speeds, and various flow rates of input oxygen.

Whilst we do not wish to be bound by the theory of the present invention, it is believed the uptake of oxygen by the organism is diffusion controlled, thus dependent on several features:

(a) The flow rate of air or oxygen enriched air;
(b) Power of the impeller to provide the driving force for dissolving oxygen in the culture broth;
(c) The overpressure and temperature (maintained at 30° C.) which determine the saturated oxygen concentration;
(d) The turn-over time in the vessel, which is related to the efficiency of the impeller in mixing the culture broth; and
(e) The viscosity and structure of the culture broth, which determines the limiting diffusion velocities.

The substrate employed in the fermentation may be of vegetable origin, for example starch, starch contaning materials or products of their hydrolysis, e.g. glucose. Sucrose, sucrose containing materials or hydrolysed sucrose i.e. invert sugar or mixtures thereof. Thus the substrate may comprise hydrolysed potato, molasses, glucose, maltose, hydrolysed bean starch or cassava. Alternative substrates of animal origin, for example, milk whey may be employed.

The non-toxic strain of Fusarium may be a strain of *Fusarium graminearum.*

The preferred non-toxic strain is our strain of *Fusarium graminearum* Schwabe (FGS), which is described and claimed together with variants and mutants thereof in GB No. 1346061, has been deposited at the Commonwealth Mycological Institute, Kew, and assigned the number IMI 145425.

GB No. 1346061 describes and claims specifically five variants of our strain of *Fusarium graminearum* Schwabe IMI 145425 namely I-7, I-8, I-9, I-15 and I-16 deposited with the Commonwealth Mycological Institute and assigned the numbers IMI 154209, IMI 154211, IMI 154212, IMI 154213 and IMI 154210 respectively.

The temperature of incubation is in general between 25° C. and 34° C., preferably around 30° C.

The process is commenced by inoculation of the nutrient broth in the fermenter with an actively growing culture of the organism FGS in vegetative growth.

The pH of the substrate medium during incubation is preferably kept within a suitable range supporting maximum growth, for example, between 3.5 to 7, preferably about pH 6.

The period of growth in batch culture under the above-mentioned conditions is dependent on the size of the inoculum and the volume of the fermenter, and is typically found to range from 20 to 48 hours for a 1300 liter vessel.

As will be well understood by those skilled in the art, sufficient quantities of substrate carbon as assimilable carbohydrate together with essential growth nutrients such as nitrogen, sulphur, phosphorus and other trace elements are maintained in the substrate medium so that growth of the organism is limited only by the oxygen available to the fungus.

In addition to the nutrients stated above the presence of one or more vitamins, such for example, as biotin, may be desirable to maintain maximum growth rate.

The substance produced according to the present invention may be isolated in any suitable manner known in the art. Thus the resulting mycelium may be recovered by separation from the nutrient broth e.g. by filtration. The substance produced according to the present invention may be texturised in the manner according to GB No. 1502445 after mixing with suitable permitted colouring and flavouring agents. The texturised material can then be formulated into products which are stored, frozen or chilled.

The fungal mycelium, because of its filamentous structure, can be used as an analogue of various meat products, particularly with the addition of flavouring and colouring materials.

The present invention will be further described with reference to the accompanying examples.

EXAMPLES

The following examples illustrate the nutrient medium flow rates and fermenter process conditions for continuous culture growth of *Fusarium graminearum* Schwabe IM 145425 under different limiting nutrients.

Examples 1 to 8 are limitations on oxygen with Example 9 being a limitation on carbon by way of comparison.

In all examples, medium components are added aseptically. Glucose syrup, magnesium sulphate, potassium sulphate, monoammonium phosphate, ferric chloride or ferrous sulphate, zinc sulphate, manganous sulphate and copper sulphate are made up together in a single nutrient medium which is sterilised at 138° C., typically for 5 to 7 minutes at 377 $kN/m^2$ pressure, cooled to ambient temperature and continuously added to a 1300 liter stainless steel vessel containing the culture broth, at the flow rate indicated. In all examples the fermenter is maintained at 30° C. and is stirred at the rate indicated by a dual impeller, comprising an 18 bladed disc turbine (diameter (D)=0.508 m) and a triple bladed sabre (D=0.7 m) in a fully baffled vessel.

Indicated levels of sterile air are passed through the vessel, and the pH of the culture is maintained at pH 6 by direct introduction of ammonia into the air feed to the vessel.

The biomass produced leaves the fermentation vessel in a steady flow, and the ribonucleic acid (RNA) reduced by the method described in GB No. 1440642. The biomass data tabulated refers to material which has been treated to reduce the RNA content by this method.

The biomass is harvested by means of a filter. The following table, shows that the mean hyphal length of the organism, and the colour, texture and odour of the harvested biomass is influenced by the limiting nutrient in the fermentation process.

Biomass AAN is a measurement of amino acid nitrogen which gives an index of the amount of protein present in the material produced.

Biomass median length is median length of hyphal strands present.

Texture is assessed and graded by a taste panel.

The yield factor on carbon is calculated as the weight of organism formed/weight of carbon substrate used.

Productivity is the weight of biomass produced in unit volume in unit time, and is calculated as the weight of biomass per liter x dilution rate. Dilution rate is the rate of flow of nutrients into the fermenter vessel divided by the vessel volume and is expressed in units of $hr^{-1}$. Over-pressure is the positive pressure in the fermenter vessel above atmospheric pressure expressed in units of $kN/m^2$. Thus, the absolute pressure in the fermenter is atmospheric pressure+over-pressure.

Examples 1–8 illustrate various fermentation conditions by which average to good eating quality material can be produced in oxygen limitation.

Examples 1 and 8 illustrate high over-pressure in the fermenter. Examples 2, 4, 5, 6 illustrate low over-pressure and Example 7 is intermediate.

Examples 1, 3 and 8 illustrate high air flow. Example 6 illustrates low air flow.

Examples 1, 7 and 8 illustrate high productivity. Examples 2, 4 and 6 illustrate low productivity.

Whilst the most desirable productivities are obtained with dilution rates in the range $0.17–0.19^{-1}$ it is posible to allow the organism to grow in oxygen limitation at dilution rates in excess of 0.25. Example 6 illustrates growth at dilution rate 0.25 $hr^{-1}$.

| | EXAMPLE NO. | | | | | | | | | |
|---|---|---|---|---|---|---|---|---|---|---|
| | 1 | 2 | 3 | 4 | 5 | 6 | 7 | 8 | 9 | Unit |
| Limitation | $O_2$ | $O_2$ | $O_2$ | $O_2$ | $O_2$ | $O_2$ | $O_2$ | $O_2$ | C | |
| Nutrients | | | | | | | | | | |
| Glucose (maize syrup) | 39.5 | 41.5 | 27.22 | 34.83 | 23.3 | 22.45 | 46.25 | 48.00 | 15.73 | g/l |

-continued

|  | EXAMPLE NO. | | | | | | | | | Unit |
|---|---|---|---|---|---|---|---|---|---|---|
|  | 1 | 2 | 3 | 4 | 5 | 6 | 7 | 8 | 9 |  |
| Mono ammonium phosphate | 2.1 | 2.1 | 1.30 | 2.26 | 1.30 | 1.30 | 1.65 | 1.39 | 1.34 | g/l |
| Potassium sulphate | 2.1 | 2.1 | 2.1 | 3.65 | 2.1 | 2.1 | 2.1 | 2.1 | 2.1 | g/l |
| Magnesium sulphate | 0.87 | 0.87 | 0.87 | 1.51 | 0.87 | 0.87 | 0.87 | 0.87 | 0.87 | g/l |
| Biotin | 0.0134 | 0.009 | 0.004 | 0.009 | 0.004 | 0.004 | 0.004 | 0.004 | 0.004 | mg/l |
| Choline | 87.0 | 87.0 | 87.0 | 113.9 | 87.0 | 87.0 | 670.0 | 456.5 | 87.0 | mg/l |
| $FeSO_4 7H_2O$ | — | — | 1.26 | 7.57 | 3.79 | 4.34 | 4.34 | 4.34 | 4.34 | mg/l |
| $FeCl_3 6H_2O$ | 3.64 | 5.94 | — | — | — | — | — | — | — | mg/l |
| $ZnSO_4 7H_2O$ | 19.30 | 26.09 | 8.7 | 15.13 | 8.7 | 8.7 | 8.7 | 8.7 | 8.7 | mg/l |
| $MnSO_4 4H_2O$ | 15.46 | 17.39 | 8.7 | 15.13 | 8.7 | 8.7 | 8.7 | 8.7 | 8.7 | mg/l |
| $CuSO_4 5H_2O$ | 1.85 | 3.48 | 0.87 | 3.03 | 0.90 | 0.87 | 0.87 | 0.87 | 0.87 | mg/l |
| Conditions |  |  |  |  |  |  |  |  |  |  |
| Flow rate | 218 | 265 | 255 | 265 | 264 | 326 | 254 | 228 | 265 | l/hr |
| Fermenter volume | 1252 | 1340 | 1280 | 1342 | 1245 | 1305 | 1350 | 1321 | 1230 | l |
| Dilution rate | 0.174 | 0.20 | 0.20 | 0.20 | 0.21 | 0.25 | 0.188 | 0.172 | 0.22 | hr |
| Cell biomass concn. | 17.9 | 9.2 | 11.1 | 10.2 | 10.7 | 8.7 | 20.7 | 21.4 | 9.8 | g/l |
| Stirrer speed | 180 | 180 | 180 | 185 | 180 | 179 | 200 | 200 | 180 | rpm |
| Air flow | 1500 | 1211 | 1316 | 1239 | 1216 | 412 | 1072 | 1112 | 1458 | l/min |
| Overpressure | 207 | 34.5 | 55 | 34.5 | 34.5 | 34.5 | 117 | 207 | 34.5 | $kN/m^2$ |
| Glucose excess | 5.5 | 17.7 | 6.2 | 13.2 | 3.9 | 5.0 | 10.8 | 7.4 | <0.1 | g/l |
| Results |  |  |  |  |  |  |  |  |  |  |
| Biomass AAN | 75.5 | 66.0 | 68.1 | 63.5 | 68.5 | 68.2 | 67.5 | 64.1 | 49.8 | mg/g |
| Biomass median length | 0.38 | 0.40 | 0.39 | 0.43 | 0.41 | 0.44 | 0.36 | 0.32 | 0.28* | mm |
| Colour | Pale Buff | Pale Buff | Buff | Buff | Buff | Buff | Dark Buff | Dark Buff | Pink Red | — |
| Texture | Good | Average | Good | Good | Av. Good | Av. Good | Average | Average | Av. Poor | — |
| Yield factor on carbon | 0.53 | 0.39 | 0.53 | 0.47 | 0.47 | 0.50 | 0.58 | 0.53 | 0.62 | — |
| Productivity | 3.11 | 1.84 | 2.22 | 2.04 | 2.25 | 2.1 | 3.89 | 3.68 | 2.16 | g/l/hr |

*(branched)

What is claimed is:

1. A process for the production of an edible protein-containing substance having linear hyphae with little or no chain-branching comprising the steps of; inoculating and operating a continuous fermentation in a fermenter at a temperature of between 25° C. and 34° C., the fermenter being under a pressure of 101 $kN/m^2$ to 505 $kN/m^2$, the fermentation occurring at a pH of 3.5 to 7, using Fusarium graminearum schwabe IMI 14525 or variants or mutants thereof, in a culture medium comprising carbohydrate, Mg K, $PO_4$, Fe, Zn, Mn and Cu ions as growth-promoting substances, all in excess, aerating the fermentation at a flow rate of 0.32 to 1.2 liters per minute per liter volume of the fermenter, such that the oxygen is the limiting nutrient but supports cell concentration in the culture without the occurrence of anaerobic growth, to provide hyphae of longer length with little or no chain-branching.

2. A process as claimed in claim 1, wherein the median length of the hyphae is 0.3 mm to 0.5 mm with little or no branching.

3. An edible protein-containing substance having linear hyphae with little or no chain-branching made by the process which comprises: inoculating and operating a continuous fermentation in a fermenter at a temperature of between 25° C. and 34° C., the fermenter being under a pressure of 101 $kN/m^2$ to 505 $kN/m^2$, the fermentation occurring at a pH of 3.5 to 7, using Fusarium graminearum schwabe IMI 14525 or variants or mutants thereof, in a culture medium comprising carbohydrate, Mg K, $PO_4$, Fe, Zn, Mn and Cu ions as growth-promoting substances, all in excess, aerating the fermentation at a flow rate of 0.32 to 1.2 liters per minute per liter volume of the fermenter, such that the oxygen is the limiting nutrient but supports cell concentration in the culture without the occurrence of anaerobic growth, to provide hyphae of longer length with little or no chain-branching.

4. An edible protein-containing substance as claimed in claim 3 wherein the median length of the hyphae is 0.3 mm to 0.5 mm with little or no branching.

* * * * *